(12) United States Patent
Ghalili

(10) Patent No.: US 10,695,301 B2
(45) Date of Patent: *Jun. 30, 2020

(54) VETERINARY CANNABINOID AND MENTHOL COMPOSITIONS AND METHODS

(71) Applicant: Babak Ghalili, New York, NY (US)

(72) Inventor: Babak Ghalili, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/419,392

(22) Filed: May 22, 2019

(65) Prior Publication Data

US 2020/0069606 A1 Mar. 5, 2020

Related U.S. Application Data

(60) Provisional application No. 62/726,713, filed on Sep. 4, 2018.

(51) Int. Cl.
| | | |
|---|---|---|
| *A61K 31/05* | (2006.01) | |
| *A61K 47/10* | (2017.01) | |
| *A61K 9/02* | (2006.01) | |
| *A61K 47/38* | (2006.01) | |
| *A61K 9/00* | (2006.01) | |
| *A61K 9/06* | (2006.01) | |

(52) U.S. Cl.
CPC ............... *A61K 31/05* (2013.01); *A61K 9/02* (2013.01); *A61K 47/10* (2013.01); *A61K 47/38* (2013.01); *A61K 9/006* (2013.01); *A61K 9/06* (2013.01)

(58) Field of Classification Search
CPC .................................. A61K 8/19; A61K 47/10
USPC ............................................. 424/52; 514/454
See application file for complete search history.

(56) References Cited

U.S. PATENT DOCUMENTS

| | | |
|---|---|---|
| 5,192,802 A | 3/1993 | Rencher |
| 5,234,957 A | 8/1993 | Mantelle |
| 7,025,992 B2 | 4/2006 | Whittle et al. |
| 8,642,645 B2 | 2/2014 | Kelly |
| 9,095,563 B2 | 8/2015 | Sekura et al. |
| 9,839,693 B2 | 12/2017 | Borja et al. |
| 10,028,904 B2 | 7/2018 | Smith et al. |
| 10,080,736 B2 | 9/2018 | Kleidon et al. |
| 2002/0197320 A1 | 12/2002 | Pena et al. |
| 2008/0112895 A1* | 5/2008 | Kottayil ............. A61K 9/08 424/46 |
| 2013/0281523 A1 | 10/2013 | Letendre et al. |
| 2016/0166498 A1* | 6/2016 | Anastassov ........... A61K 8/19 424/52 |
| 2016/0346339 A1 | 12/2016 | Finley et al. |
| 2017/0021029 A1 | 1/2017 | Raber et al. |
| 2017/0239359 A1 | 8/2017 | Borja et al. |
| 2017/0266153 A1 | 9/2017 | Levy et al. |
| 2017/0290870 A1 | 10/2017 | Schaneville |
| 2017/0368020 A1 | 12/2017 | Estey et al. |

FOREIGN PATENT DOCUMENTS

| | | |
|---|---|---|
| EP | 0185968 A2 | 7/1986 |
| WO | 2017059088 A1 | 4/2017 |

OTHER PUBLICATIONS

RobHolland.com, "GLYCERIN." www.robholland.conn/Nursing/Drug_Guide/data/monographframes/G019.html. Published online Jul. 2, 2010. (Year: 2010).*
Abualhasan et al., "GC Method Validation for the Analysis of Menthol in Suppository Pharmaceutical Dosage Form." International Journal of Analytical Chemistry. Published Mar. 6, 2017. (Year: 2017).*
Iscan et al., "Antimicrobial Screening of Mentha piperita Essential Oils." J. Agric. Food Chem. 2002, 50, 3943-3946. (Year: 2002).*
International Search Report and Written Opinion of the International Searching Authority, Application No. PCT/US2019/048695, dated Jan. 17, 2020, 20 pages.
"What Does Full Spectrum Mean?" Extract Labs, Jul. 31, 2019, retrieved on Dec. 30, 2019 from https://www.extractlabs.com/cbd-guides/what-does-full-spectrum-mean/, 6 pages.

\* cited by examiner

*Primary Examiner* — Walter E Webb
(74) *Attorney, Agent, or Firm* — Ziegler IP Law Group LLC

(57) ABSTRACT

The present disclosure relates to compositions, including, hydrogel compositions useful as topical oral analgesics including cannabinoids and menthol in a composition formulated to be administrable to a non-human animal rectally as a suppository.

18 Claims, 2 Drawing Sheets

VETERINARY CANNABINOID AND MENTHOL COMPOSITIONS AND METHODS

CROSS-REFERENCE TO RELATED APPLICATIONS

This application claims priority to and the benefit of U.S. Provisional Patent Application Ser. No. 62/726,713 filed Sep. 4, 2018, the disclosure of which is incorporated herein by reference in its entirety.

FIELD

The aspects of the present disclosure relate to compositions including active agents such as cannabinoids and menthol.

BACKGROUND

There is a need for novel treatments for pain and inflammation, particularly in the treatment of oral and dental pain. Some current agents may be ineffective and can, for example, come with unacceptable side effects. Furthermore, there is a growing concern about the overuse of opioid pain treatments.

Hydrogels can be used as a vehicle for the delivery of drugs and other therapeutically active agents. They refer to a network of hydrophilic polymer chains that are generally found as a colloidal gel in which water is the dispersion medium. Hydrogels are highly absorbent (they can contain over 99.9% water) natural or synthetic polymers and can also possess a degree of flexibility very similar to natural tissue, due to their significant water content ("Terminology of polymers and polymerization processes in dispersed systems (IUPAC Recommendations 2011)". Pure and Applied Chemistry 83 (12): 2229-2259. 2011).

Hydrogels are characterized by the inclusion of water which acts to disperse the polymer into a colloidal mass. Unfortunately, the presence of water limits the utility of these products to water sensitive materials or environments where moisture is contraindicated. The physical properties of water also dictate the physical properties of the hydrogel, such as reactivity to acids and bases. Thus, there are applications, including the delivery of drugs and other therapeutically active agents, where anhydrous hydrogels (i.e., hydrogels without the aqueous limitations) may be preferred.

BRIEF DESCRIPTION OF THE DRAWINGS

The accompanying drawings illustrate presently preferred embodiments of the present disclosure, and together with the general description given above and the detailed description given below, serve to explain the principles of the present disclosure.

SUMMARY

Figure 1:
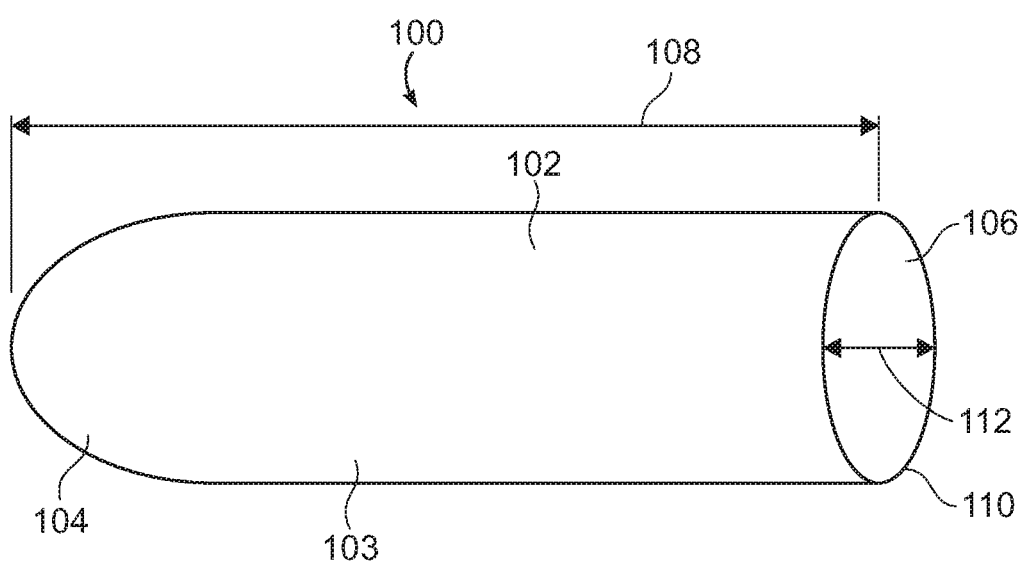
FIG. 1 is a perspective view of an embodiment of the present disclosure.

In one embodiment, a composition is provided. The composition includes a biocompatible polymer in an amount of from about 1 wt % to about 25 wt %, a polyalcohol in an amount of from about 1 wt % to about 45 wt %, a veterinary effective amount of at least one cannabinoid and a veterinary effective amount of menthol, wherein the composition is formulated to be administrable to a non-human animal rectally as a suppository.

In another embodiment, a composition is provided. The composition includes sodium carboxymethyl cellulose in an amount of from about 1 wt % to about 25 wt %, glycerin polyalcohol in an amount of from about 1 wt % to about 45 wt %; CBD in an amount of from about 0.1 wt % to about 10 wt %. including a unit dose of CBD in an amount ranging from about 5 mg. to about 1500 mg. and menthol is in an amount of from about 0.1 wt % to about 14 wt % including a unit dose of the menthol in an amount ranging from about 30 mg. to about 1500 mg, wherein the composition is formulated to be administrable to a non-human animal rectally as a suppository.

In another embodiment, a method of treating inflammation in a non-human mammal using a therapeutic composition is provided. The therapeutic composition includes sodium carboxymethyl cellulose including minimal residual water in an amount of from about 1 wt % to about 25 wt %, anhydrous glycerin polyalcohol in an amount of from about 1 wt % to about 45 wt %, CBD in a unit dose amount of from about about 5 mg. to about 1500 mg. and menthol in a unit dose amount of from about 30 mg. to about 1500 mg. The method includes the method comprising administering the therapeutic composition into a rectal cavity of the non-human mammal.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The aspects of the disclosed embodiments relate to an anhydrous hydrogel for the delivery of an active agent(s). Particularly important active agents are those that are moisture sensitive. The aspects of the disclosed embodiments also relate to processes for the preparation of, intermediates used in the preparation of, compositions (e.g., pharmaceutical, medical device cosmetic, industrial) containing and the uses of such hydrogels in the treatment of disorders or application of specified agents to a surface.

One specific embodiment of the present disclosure relates to compositions comprising an active agent (including acceptable salt thereof) pharmaceutical composition. Accordingly, in one embodiment, the present disclosure relates to a pharmaceutical composition comprising an active agent, a pharmaceutically acceptable carrier and, optionally, additional medicinal or pharmaceutical agent(s)

Active agents include pharmaceutical agents such as analgesics, decongestants, bronchodilators and other antiasthmatic agents, cardiovascular agents such as beta-blockers, ACE inhibitors, diuretics, antithrombics, etc., diabetic agents, antihistamines, anesthetics, antifungals, antinauseants, antiemetics, antibacterial agents, antifungal agents, corticosteroids, neurological agents, anti-inflammatories, vaccines, biological agents (such as Humera, Enbrel and Remicade), wound healing agents and anticonvulsants. Vitamins (particularly A, C, D and E) are a particular embodiment of an active agent. The concentration of the active ingredient in the gel base is, of course, dependent on the identity of the active agent, the condition and patient being treated and the potency desired.

One group of particularly interesting active agents include pharmaceutical agents that are moisture sensitive such as biologicals, enzymes, proteins (and fragments thereof). Other moisture sensitive pharmaceutical agents include Adderall, alprazolam, gemifloxacin, hydromorphone and zolmitriptan.

Another embodiment relates to antifungal active agents such as Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, and Micafungin.

Another embodiment of the present disclosure relates to wart removal compounds such as salicylic acids. Such treatments are of specific interest due to heightened response to the anhydrous medium of the hydrogel.

One specific embodiment relates to wound healing agents and products (such as gauze, bandage, and synthetic skin). Such agents include aloe, benzyl alcohol, coagulants (such as styptic, chitosan, vitamin K, phytomenadione, menadione, etamsylate, carbazochrome Batroxobin), ferric sulfate, ticosan, becaplermin, antimicrobial agents (including antibiotics such as gentamycin, polymyxin B, zinc bacitracin, metronidazole, ofloxacin, minocycline, hydrocortisone, triamcinolone and tetracycline), antifungals, silver, povidone-iodine, polyhexamethylene biguanide, dialkylcarbamoylchloride, lactoferrin, growth factors (such as epidermal growth factor (EGF), platelet derived growth factor (PDGF), fibroblast growth factor (FGF), transforming growth factor (TGF-b1), insulin-like growth factor (IGF-1), human growth hormone, granulocyte macrophage colony stimulating (GM-CSF)).

Another embodiment relates to scar healing agents such as vitamins, aloe vera, and benzyl alcohol.

Active agents also includes cosmetic agents such as caffeine, sunscreens (such as butyl methoxydibenzoylmethane, oxybenzone, bumetrizole, ecamsule, phenylbenzimidazole sulfonic acid, ethylhexyl methoxycinnamate, menthyl anthranilate, octocrylene, para-aminobenzoic acid (PABA), and Tinosorb M), anti-inflammatories (such as salicylates), anti-acne agents (such as (isotretinoin, Benzamycin, clindamycin, Erythromycin, minocycline and tretinoin), vitamins (particularly vitamins C and E, Biotin), ubiquinone, retinoids, Minoxidyl, Zinc pyrithion, ketoconazole, allantoin, herbal extracts (such as Passion Fruit extract (*Passiflora Edulis*), Red rose extract, Raspberry extract (*Rubus ldaeus*), Yucca herbal extract, Aloe vera leaf gel, Tea tree oil (*Melaleuca Altemifolia*), Peppermint leaf oil, Spearmint leaf oil, Wintergreen leaf oil (*Gaultheria Procumbens*), Lavender oil, Cinnamon leaf oil, Lemon peel oil, Valencia orange peel oil, Pink grapefruit peel oil, Roman chamomile oil (*Anthemis Nobilis* Flower Oil), and Jasmine oil), protein hydrolysates (i.e. short protein fragments that are still called "peptides") and skin lightening agents.

One particular cosmetic agent of interest is coenzyme Q10 (Co Q10), also known as ubiquinone, ubidecarenone, coenzyme Q, and abbreviated at times to CoQ10, CoQ or Q10. Ubiquinone is a 1,4-benzoquinone, where Q refers to the quinone chemical group, and 10 refers to the number of isoprenyl chemical subunits in its tail.

Active agents also include breath fresheners and oral hygienics such as triclosan, chlorhexidine gluconate and complexed metals such as Ag, Cu, Zn or Sn. Dental adhesives such as Gantrez MS-955 polymer (a mixed sodium and calcium salt of methyl vinyl ether and maleic anhydride copolymer supplied as a powder) are also active agents. The formulations of the present disclosure are particularly suitable as dental adhesives demonstrating significant holding power over other adhesive technologies. The formulations of the present disclosure are also useful in the treatment of dry mouth and dry vagina syndromes.

Active agents also include odor reducing agents such as cyclodextrins, sodium bicarbonate, activated charcoal, potassium bicarbonate, zinc undecylenate, undecylenic acid methyl ester, chlorophyll copper complex (CCC), Grillocin, bismuth compounds such as bismuth salicylate (BiS), bismuth subgallate (BiG) and bismuth citrate (BiC), and esters of 3-methyl-2-hexenoic acid.

The hydrogels of the present disclosure are also useful for treatment of nipple disorders, delivery of laxatives and anti-diarrheas such as loperamide and bismuth subsalicylate (such as Kaopectate and Pepto-Bismol).

The hydrogels of the present disclosure are also useful as food additives which can preserve flavor and aroma.

Flavors and fragrances are well known in the food and cosmetic industry. Many of these compounds are susceptible to hydrolytic deactivation. Formulations of such flavor and fragrance compounds in the hydrogels of the present disclosure have surprising shelf life and release kinetics.

The formulations of the present disclosure are also useful sensors, electrodes and circuits. The use of these hydrogels in defibrillators is advantageous due to the resilience of the actives in a non-aqueous base.

The formulations of the present disclosure are also useful in the field of veterinary medicine for the administration of active agents to pets and farm animals.

The formulations of the present disclosure are also useful as diagnostic tools for the identification of infection, metal contamination and humidity.

Another embodiment of the present disclosure relates to compositions used as a rheology modifier for gel and liquid formulations.

The aspects of the present disclosure relate to compositions used to relieve pain (i.e., analgesics) and/or inflammation, methods of making such compositions and methods of using such compositions including, for example, oral or topically applied (e.g., to skin or another body part, e.g., rectally) compositions including pharmaceutical compositions, including analgesic and/or anti-inflammatory pharmaceutical compositions for the treatment of pain and/or inflammation, that contain a pharmaceutically effective amount of a pharmaceutically acceptable and effective cannabinoid, menthol and a pharmaceutically acceptable carrier. Such compositions may also include, for example, oral care compositions, including oral care analgesic and/or anti-inflammatory compositions for the treatment of oral or dental pain and/or inflammation, that contain a pharmaceutically effective amount of an oral or dental acceptable and effective cannabinoid, menthol and an oral or dental acceptable carrier. Such compositions may also include, for example, analgesic and/or anti-inflammatory pharmaceutical compositions for the treatment of pain and/or inflammation that contain a pharmaceutically effective amount of a pharmaceutically acceptable and effective cannabinoid, menthol and a pharmaceutically acceptable carrier. Such compositions may also include, for example, oral care analgesic and/or anti-inflammatory compositions for the treatment of oral or dental pain and/or inflammation, including oral care analgesic and/or anti-inflammatory compositions, that contain a pharmaceutically effective amount of an oral or dental acceptable and effective cannabinoid, menthol and an oral or dental acceptable carrier.

The combination of cannabinoid and menthol into a single therapeutic composition, for example, a hydrogel vehicle, can provide improved and better focused delivery of the actives to a patient than separately applying the cannabinoid and menthol separately (to different areas of the body or layered one on top of another) without the hydrogel vehicle.

The aspects of the present disclosure also relate to compositions used to relieve pain (i.e., analgesics) and/or inflammation, methods of making such compositions and methods of using such compositions including, for example, veterinary care compositions including veterinary pharmaceutical compositions, including analgesic veterinary pharmaceutical compositions for the treatment of pain, that contain a veterinary pharmaceutically effective amount of a veterinary pharmaceutically acceptable and effective cannabinoid, menthol and a veterinary pharmaceutically acceptable carrier. Such compositions may also include, for example, veterinary care compositions, including veterinary care analgesic compositions for the treatment of pain, that contain a veterinary pharmaceutically effective amount of a veterinary acceptable and effective cannabinoid, menthol and a veterinary acceptable carrier. Such compositions may also include, for example, veterinary analgesic pharmaceutical compositions for the treatment of pain that contain a veterinary pharmaceutically effective amount of a veterinary pharmaceutically acceptable and effective cannabinoid, menthol and a veterinary pharmaceutically acceptable carrier. Such compositions may also include, for example, veterinary analgesic compositions for the treatment of pain, including veterinary analgesic compositions, that contain a veterinary pharmaceutically effective amount of a veterinary acceptable and effective cannabinoid, menthol and a veterinary acceptable carrier.

The above veterinary compositions, methods, etc. the term "veterinary" includes non-human animals including small animals, including, for example, dogs and cats, and large animal veterinary including, for example, equine animals (e.g. horses) and bovine animals (e.g., cows).

The combination of cannabinoid and anesthetic into a single therapeutic composition, for example, a hydrogel vehicle, can provide improved and better focused delivery of the actives to a patient than separately applying the cannabinoid and anesthetic separately (to different areas of the body or layered one on top of another) without the hydrogel vehicle.

Orally administered including oral care and other pharmaceutical compositions include products which, in the ordinary course of usage, can be swallowed or chewed (e.g., to deliver the therapeutic in the body past the oral cavity), or are not intentionally swallowed initially for purposes of systemic administration of particular therapeutic agents, but is rather retained in the oral cavity or the tissues thereof for a time sufficient to be effective for purposes of therapeutic activity within the oral cavity and surfaces and tissues therein. After being present in the oral cavity for a time sufficient to be effective for purposes of therapeutic activity, they can be removed from the oral cavity or swallowed or chewed and pass through the digestive system for removal. Oral cavity includes teeth, tissues (including mucous membranes and cheek tissue in the oral cavity) and the surfaces thereof present in mouth. Teeth, as used herein, refers to natural teeth as well as artificial teeth or dental prosthesis. The composition may, for example, be administered to patients with oral pain, such as tooth pain, and pain from gums or cheeks following dental procedures, as wells as patients with bleeding gums or areas in the mouth that are suspect to infection.

"Pain" as referred to herein for the composition and method embodiments of the current disclosure and for which an analgesic or pain relieving or pain treating composition or component thereof treats includes, but is not limited to local pain, systemic pain, oral pain, dental pain and general pain, regardless of the location on the body to which the embodiment of the current disclosure is administered.

"Anti-inflammatory" as referred to herein for the composition and method embodiments of the current disclosure and for which an anti-inflammatory composition or component thereof treats includes, but is not limited to local inflammation, systemic inflammation, oral inflammation, dental inflammation and general inflammation, regardless of the location on the body to which the embodiment of the current disclosure is administered.

Cannabinoids are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure.

Examples of phytocannabinoids include Cannabidiol (CBD) including, for example, CBD oil, Cannabinol (CBN) and tetrahydrocannabinol (THC), the latter being a known psychotropic compound and the first two being non-psychotropic. *Cannabis* plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and have minimal levels of THC (less than 0.3%). Examples of oral or pharmaceutically effective cannabinoids include CBD (for example, CBD oil), Cannabinoid, including, for example, phytocannabinoids including CBD, can be in an amount of about 0.1 wt % to about 20 wt %, about 0.1 wt % to about 10 wt %, about 0.5 wt % to about 6 wt % or about 5.7 wt %. CBD can be in an amount of about 0.1 wt % to about 20 wt %, about 0.1 wt % to about 10 wt %, about 0.5 wt % to about 5 wt %, about 0.5 wt % to about 2 wt % or about 1.9 wt %. Unit dosage formulations of the embodiments of the present disclosure can include cannabinoid, for example, a phytocannabinoid (including for example, CBD) in the amount of about 2 mg. to about 60 mg., about 5 mg. to about 30 mg., about 5 mg to about 15 mg. about 15 mg. to about 30 mg. or about 30 mg. to about 45 mg. Unit dosage formulations of the embodiments of the present disclosure can include CBD in the amount of about 2 mg. to about 30 mg., about 5 mg. to about 30 mg., about 5 mg. to about 15 mg., about 15 mg. to about 30 mg. or about 10 mg. Unit doses of CBD oil content can include an amount of about 2 mg. to about 60 mg. An effective amount of cannabinoid includes an analgesic, pain relieving, pain treating or anti-inflammatory amount of cannabinoid. An effective amount can also include a veterinary effective amount of CBD for the aforementioned maladies.

For embodiments of the present disclosure including veterinary compositions (including rectal delivery systems including suppositories) and methods, unit dosage formulations of the embodiments of the present disclosure can include cannabinoid, for example, a phytocannabinold (including for example, CBD) in the amount of about 5 mg. to about 1500 mg., about 5 mg. to about 20 mg. (e.g., small animals), about 100 mg. to about 1500 mg. (e.g., large animals), about 500 mg. to about 1500 mg., about 1000 mg. or about 40 mg/100 kg of animal weight and unit dosage formulations of the embodiments of the present disclosure can include CBD in the amount of about 5 mg. to about 1500 mg., about 5 mg. to about 20 mg. (e.g., small animals), about 100 mg. to about 1500 mg. (e.g., large animals), about 500 mg. to about 1500 mg., about 1000 mg. or about 40 mg/100 kg of animal weight.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil) that include one or a plurality of phytocannabinoids.

Menthol is an active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) when administered to a patient. Furthermore, menthol is a vasodilator that can accelerate the transport of active in the circulatory system. In a rectal delivery system, menthol may not only reduce inflammation and pain, but also produce a cooling, soothing effect. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can be in an amount of about 0.1 wt % to about 20 wt %, about 0.1 wt % to about 10 wt %, about 1 wt % to about 20 wt %, about 0.1 wt % to about 14 wt %, about 0.1 wt % to about 1 wt %, about 2 wt % to about 9 wt % about 0.62 wt %. Unit dosage formulations of the embodiments of the present disclosure can include menthol in the amount of about 2 mg. to about 20 mg., about 2 mg. to about 10 mg., about 2 mg. to about 4 mg., about 3 mg. to about 4 mg., about 5 mg. to about 7 mg., about 8 mg. to about 10 mg., about 4 mg. to about 8 mg. or about 5 mg. to about 7 mg.

For embodiments of the present disclosure including veterinary compositions (including rectal delivery systems including suppositories) and methods, unit dosage formulations of the embodiments of the present disclosure can include menthol in the amount of about 30 mg. to about 1500 mg, about 30 mg to about 100 mg, about 100 mg to about 200 mg, about 200 mg to about 450 mg., about 450 mg to about 6000 mg., about 600 mg to about 800 mg., about 800 mg to about 1100 mg., about 1100 mg to about 1500 mg. An effective amount of menthol includes an anesthetic, pain reducing (e.g., analgesic) or anti-inflammatory effective amount of menthol. An effective amount can also include a veterinary effective amount of menthol for the aforementioned maladies.

For embodiments of the present disclosure including veterinary compositions (including rectal delivery systems including suppositories) and methods, unit dosage formulations of the embodiments of the present disclosure can include the following for example:

Hemp Oil

For animals 2-6 lbs 1.0 mg to 3.0 mg
7-12 lbs 4.0 mg to 6.0 mg
13-16 lbs 7.0 mg to 9.0 mg
17-20 lbs 10.0 mg to 12.0 mg
21-26 lbs 13.0 mg to 15.0 mg
27-32 lbs 16.0 mg to 18.0 mg
33-40 lbs 19.0 mg to 22.0 mg
41-50 lbs 23.0 mg to 26.0 mg
51-60 lbs 27.0 mg to 30.0 mg For menthol, can be about 15% higher than the dose of hemp oil.

The aspects of the present disclosure also relate to hydrogels, for example, an anhydrous hydrogel for the delivery of, for example, pharmaceutical compositions, including analgesic pharmaceutical compositions, that contain a pharmaceutically effective amount of a pharmaceutically acceptable and effective cannabinoid and a pharmaceutically effective amount of menthol and oral care compositions, including oral care analgesic compositions, that contain a pharmaceutically effective amount of an oral or dental acceptable and effective cannabinoid and a pharmaceutically effective amount of menthol. Hydrogels including anhydrous hydrogels are disclosed in U.S. Pat. No. 9,839,693, Borja, et al., entitled "Anhydrous Hydrogel Compositions and Delivery System," the disclosure of which is hereby incorporated by reference in its entirety.

Embodiments of the present disclosure include hydrogels that can be formed by combining a biocompatible polymer with a polyalcohol followed by the addition of an energy source such as heat or radiation. Some embodiments of the present disclosure include hydrogels that do not dry out, or have minimal drying out, or change shape upon standing. They are also resistant to so called "cold creep" upon standing.

An embodiment of the present disclosure relates to a hydrogel or an anhydrous hydrogel composition comprising a biocompatible polymer, a polyalcohol, a veterinary pharmaceutically effective amount of a pharmaceutically acceptable and effective cannabinoid, for example, a phytocannabinoid, and a veterinary pharmaceutically effective amount of a pharmaceutically acceptable and effective menthol.

Another embodiment of the present disclosure relates to a hydrogel or an anhydrous hydrogel analgesic composition comprising a biocompatible polymer, a polyalcohol, a veterinary pain reducing (e.g., analgesic and/or anesthetic) and/or anti-inflammatory pharmaceutically effective amount of a pharmaceutically acceptable and effective cannabinoid, for example, a phytocannabinoid, and a veterinary pain reducing (e.g., analgesic and/or anesthetic) and/or anti-inflammatory pharmaceutically effective amount of a pharmaceutically acceptable and effective menthol.

Another embodiment of the present disclosure relates to a hydrogel or an anhydrous hydrogel composition comprising a veterinary pharmaceutically acceptable biocompatible polymer, a veterinary pharmaceutically acceptable polyalcohol, a veterinary pain reducing (e.g., analgesic and/or anesthetic) and/or anti-inflammatory pharmaceutically effective amount of a pharmaceutically acceptable and effective cannabinoid, for example, a phytocannabinoid, and a veterinary pain reducing (e.g., analgesic and/or anesthetic) and/or anti-inflammatory pharmaceutically effective amount of a pharmaceutically acceptable and effective menthol.

Another embodiment of the present disclosure relates to a hydrogel or an anhydrous hydrogel analgesic and/or anti-inflammatory composition comprising a pharmaceutically acceptable biocompatible polymer, a pharmaceutically acceptable polyalcohol, a pain reducing (e.g., analgesic and/or anesthetic) and/or anti-inflammatory pharmaceutically effective amount of a pharmaceutically acceptable and effective cannabinoid, for example, a phytocannabinoid, and a pain reducing (e.g., analgesic and/or anesthetic) and/or anti-inflammatory pharmaceutically effective amount of a pharmaceutically acceptable and effective menthol.

Another embodiment of the present disclosure relates to a hydrogel or an anhydrous hydrogel analgesic and/or anti-inflammatory composition comprising a pharmaceutically acceptable biocompatible polymer, a pharmaceutically acceptable polyalcohol, a pain reducing (e.g., analgesic and/or anesthetic) and/or anti-inflammatory pharmaceutically effective amount of an oral or dental acceptable and effective cannabinoid, for example, a phytocannabinoid, and a pain reducing (e.g., analgesic and/or anesthetic) and/or anti-inflammatory pharmaceutically effective amount of an oral or dental acceptable and effective menthol.

Examples of suitable biocompatible polymers, including pharmaceutically acceptable biocompatible polymers, can include sodium carboxymethylcellulose, pectin, sodium alginate, sodium/calcium alginate, polylactic acid, chitosan, carageenan, xanthan, gellan, polyaspartic acid, polyglutamic acid, hyaluronic acid or salts or derivatives thereof. A preferred biocompatible polymer is sodium carboxymethylcellulose.

Examples of suitable polyalcohols, including pharmaceutically acceptable biocompatible polyalcohols, can include alcohols containing 2 to 10 carbon atoms and 2 to 7 hydroxyl groups including, for example, ethylene glycol, 1,2-propylene glycol, 1,4-butylene glycol, glycerine, erythrit (meso-1,2,3,4-Butantetrol), sorbit, mannit, methylglucoside, diglycerine, triglycerine and/or pentaerythrit. A preferred polyol is glycerin.

An embodiment of the present disclosure relates to a hydrogel or an anhydrous hydrogel composition comprising glycerin, sodium carboxymethyl cellulose, a pharmaceutically effective amount of a pharmaceutically acceptable and effective cannabinoid, for example, a phytocannabinoid, and a pharmaceutically effective amount of a pharmaceutically acceptable and effective menthol.

Another embodiment of the present disclosure relates to a hydrogel or an anhydrous hydrogel analgesic composition comprising glycerin, sodium carboxymethyl cellulose, a pain reducing (e.g., analgesic) and/or anti-inflammatory pharmaceutically effective amount of a pain reducing (e.g., analgesic) and/or anti-inflammatory pharmaceutically acceptable and effective cannabinoid, for example, a phytocannabinoid, and a pharmaceutically effective amount of a pain reducing (e.g., analgesic and/or anesthetic) and/or anti-inflammatory pharmaceutically acceptable and effective menthol.

Glycerin (also commonly known as glycerol, glycerin, propanetriol and 1,2,3-trihydroxypropane) is a widely used commercial product with over a million tons produced annually. High purity glycerin (>99.5%) is known. Anhydrous glycerin refers to glycerin with minimal residual water. United States Pharmacopeia (USP) describes one recognized standard of high purity anhydrous glycerin (>99.0-101.0%) as containing not more than 0.5% water. The otic therapeutic Auralgan is described as containing USP glycerin with not more than 0.6% water. The present disclosure includes such glycerin containing 0.5% and lower residual water. Specific embodiments include 99.7% (weight) water free, 99.8%, 99.9% and absolute (100%) (i.e. less than 0.3%, 0.2%, 0.1% residual water).

Sodium carboxymethyl cellulose is a cellulose derivative with carboxymethyl groups ($-CH_2-CO_2H$) bound to some of the hydroxyl groups of the glucopyranose monomers that make up the cellulose backbone. Commercial polymer products are typically categorized by average glucopyranose chain length molecular weights (MW) of 70,000, 80,000, 90,000 g/m. Anhydrous sodium carboxymethyl cellulose refers to a product with minimal residual water, such as, sodium carboxymethyl cellulose containing less than 0.5% residual water, less than 0.3% residual water and less residual water. Specific embodiments can include 99.5%, 99.7% (weight) water free, 99.8%, 99.9% and absolute (100%) (i.e. less than 0.5%, 0.3%, 0.2%, 0.1% residual water).

The combination of anhydrous glycerin and anhydrous sodium carboxymethyl cellulose (CMC) yields an anhydrous material that upon addition of heat (or radiation) is transformed into an anhydrous hydrogel. Unit dosage formulations of the embodiments of the present disclosure may be prepared by the addition of about 2 mg. to about 20 mg. of cannabinoid, about 2 mg. to about 60 mg., about 5 mg. to about 30 mg., about 5 mg. to about 15 mg., about 15 mg. to about 30 mg. or about 30 mg. to about 45 mg. Unit dosage formulations of the embodiments of the present disclosure can include CBD in the amount of about 2 mg. to about 30 mg., about 5 mg. to about 30 mg., about 5 mg. to about 15 mg., about 15 mg. to about 30 mg. or about 10 mg., for example, a phytocannabinold, and about 2 mg. to about 20 mg., about 2 mg. to about 10 mg., about 2 mg. to about 4 mg., about 3 mg. to about 4 mg., about 5 mg. to about 7 mg., about 8 mg. to about 10 mg., about 4 mg. to about 8 mg. or about 5 mg. to about 7 mg. of menthol with glycerin and CMC is likewise transformed into a homogeneous hydrogel upon the addition of heat. These products, anhydrous hydrogels, can have less than 0.5% water, more preferably less than 0.4% water, more preferably less than 0.3% water.

Such anhydrous hydrogels are hygroscopic and thus may be subject to post production processes that maintain the product in a water-free state. One such method is coating of the hydrogel with a hydrophobic layer. Alternate methods include storage of products in moisture free containers. Many of the products once formed may be stable enough to atmospheric moisture such that they can be stored in standard delivery apparatus.

An embodiment of the present disclosure relates to an anhydrous hydrogel composition comprising anhydrous glycerin, anhydrous sodium carboxymethyl cellulose, a pharmaceutically effective amount of a pharmaceutically acceptable and effective cannabinoid, for example, a phytocannabinoid, and a pharmaceutically effective amount of a pharmaceutically acceptable and effective menthol.

Another embodiment of the present disclosure relates to an anhydrous hydrogel analgesic composition comprising anhydrous glycerin, anhydrous sodium carboxymethyl cellulose, a pain reducing (e.g., analgesic and/or anesthetic) and/or anti-inflammatory pharmaceutically effective amount of a pain reducing (e.g., analgesic and/or anesthetic) and/or anti-inflammatory pharmaceutically acceptable and effective cannabinoid, for example, a phytocannabinoid, and a pain reducing (e.g., analgesic and/or anesthetic and/or anesthetic) and/or anti-inflammatory pharmaceutically effective amount of a pain reducing (e.g., analgesic and/or anesthetic) and/or anti-inflammatory pharmaceutically acceptable and effective menthol.

Another embodiment of the present disclosure relates to an anhydrous hydrogel analgesic composition comprising anhydrous glycerin, anhydrous sodium carboxymethyl cellulose, a pain reducing (e.g., analgesic) and/or anti-inflammatory pharmaceutically effective amount of an oral or dental acceptable and effective cannabinoid, for example, a phytocannabinoid, and a pain reducing (e.g., analgesic and/or anesthetic) and/or anti-inflammatory pharmaceutically effective amount of a pharmaceutically acceptable and effective menthol.

In one embodiment of the present disclosure, the hydrogel comprises the biocompatible polymer (CMC) in an amount of 1 to about 50 wt %, the polyalcohol (Glycerin) in an amount of 1 wt % to about 20 wt %, cannabinoid, for example, phytocannabinoids, in an amount of about 0.1 wt % to about 20 wt %, about 0.1 wt % to about 10 wt % or about 0.5 wt % to about 5 wt % and menthol in an amount of about 0.1 wt % to about 20 wt %, about 1 wt % to about 20 wt %, %, about 0.1 wt % to about 10 wt %, about 0.1 wt % to about 14 wt %, about 0.1 wt % to about 1 wt % or about 2 wt % to about 9 wt %.

In another embodiment of the present disclosure, unit dosage form (e.g., a patch) amounts may include about 2 mg. to about 60 mg., about 5 mg. to about 30 mg., about 5 mg. to about 15 mg., about 15 mg. to about 30 mg. or about 30 mg. to about 45 mg. of cannabinoid, for example, CBD, and about 2 mg. to about 20 mg., about 2 mg. to about 10 mg., about 2 mg. to about 4 mg., about 3 mg. to about 4 mg., about 5 mg. to about 7 mg., about 8 mg. to about 10 mg., about 4 mg. to about 8 mg. or about 5 mg. to about 7 mg. of menthol.

In another embodiment of the present disclosure, unit dosage form (e.g., a patch) amounts may include about 2 mg. to about 30 mg., about 5 mg. to about 30 mg., about 5 mg. to about 15 mg., about 15 mg. to about 30 mg. or about 10 mg. of CBD, and about 2 mg. to about 20 mg., about 2 mg. to about 10 mg., about 2 mg. to about 4 mg., about 3 mg. to about 4 mg., about 5 mg. to about 7 mg., about 8 mg. to about 10 mg., about 4 mg. to about 8 mg. or about 5 mg. to about 7 mg. of menthol.

One embodiment of an anhydrous hydrogels of the present disclosure may generally comprise about 0.1 wt. % to about 50 wt. % of an anhydrous carboxymethyl cellulose such as carboxymethyl cellulose, 99.5-50% anhydrous glycerin (w/w), cannabinoid, for example, phytocannabinoids, in an amount of about 0.1 wt % to about 20 wt %, about 0.1 wt % to about 10 wt % or about 0.5 wt % to about 5 wt % and menthol in an amount of about 0.1 wt % to about 20 wt %, %, about 0.1 wt % to about 10 wt %, about 1 wt % to about 20 wt %, about 0.1 wt % to about 14 wt %, about 0.1 wt % to about 1 wt % or about 2 wt % to about 9 wt %.

Another embodiment of the present disclosure relates to an anhydrous hydrogel composition, comprising (a) an anhydrous hydrogel including 5-30% by weight of a biocompatible polymer, which is sodium carboxymethyl cellulose including minimal residual water and 70-95% by weight anhydrous glycerin, wherein the anhydrous hydrogel is solid or semi-solid hydrogel having less than 0.5% water; and (b) cannabinoid, for example, phytocannabinoids, in an amount of about 0.1 wt % to about 20 wt %, about 0.1 wt % to about 10 wt % or about 0.5 wt % to about 5 wt % and menthol in an amount of about 0.1 wt % to about 20 wt %, about 0.1 wt % to about 1 wt %, about 0.1 wt % to about 10 wt %, about 1 wt % to about 20 wt %, about 0.1 wt % to about 14 wt %, about 0.1 wt % to about 1 wt % or about 2 wt % to about 9 wt %.

Another embodiment of the present disclosure relates to an anhydrous hydrogel composition, comprising an anhydrous hydrogel including 5-30% by weight of a biocompatible polymer, which is sodium carboxymethyl cellulose including minimal residual water and 70-95% by weight anhydrous glycerin, wherein the anhydrous hydrogel is solid or semi-solid hydrogel having less than 0.5% water; cannabinoid, for example, CBD, in an amount of about 0.1 wt % to about 20 wt %, about 0.1 wt % to about 10 wt % or about 0.5 wt % to about 5 wt % and menthol in an amount of about 0.1 wt % to about 20 wt %, about 1 wt % to about 20 wt %, about 0.1 wt % to about 14 wt %, about 0.1 wt % to about 1 wt % or about 2 wt % to about 9 wt %.

In another embodiment of the present disclosure, the hydrogel comprises the biocompatible polymer (CMC including anhydrous CMC that includes minimal residual water) in an amount of 1 to about 25 wt %, about 1 wt % to about 20 wt %, about 6 wt % to about 14 wt %, about 15 wt % to about 20 wt %, about 1 wt % to about 6 wt %, about 7 wt % to about 13 wt % or about 14 wt % to about 20 wt %; the polyalcohol (Glycerin including anhydrous glycerin) in an amount of 1 to about 45 wt %, about 1 wt % to about 12 wt %, about 12 wt % to about 23 wt %, about 23 wt % to about 34 wt %, about 34 wt % to about 45 wt %, about 12 wt % to about 34 wt % or about 30 wt % to about 40 wt %; cannabinoid, for example, phytocannabinoids, in an amount of about 0.1 wt % to about 20 wt %, about 0.1 wt % to about 10 wt % or about 0.5 wt % to about 5 wt %; and menthol in an amount of about about 0.1 wt % to about 20 wt %, about 1 wt % to about 20 wt %, about 0.1 wt % to about 14 wt %, about 0.1 wt % to about 1 wt % or about 2 wt % to about 9 wt %.

In another embodiment of the present disclosure, the hydrogel comprises the biocompatible polymer (CMC including anhydrous CMC that includes minimal residual water) in an amount of 1 to about 25 wt %, about 1 wt % to about 20 wt %, about 6 wt % to about 14 wt %, about 15 wt % to about 20 wt %, about 1 wt % to about 6 wt %, about 7 wt % to about 13 wt % or about 14 wt % to about 20 wt %; the polyalcohol (Glycerin including anhydrous glycerin) in an amount of 1 to about 45 wt %, about 1 wt % to about 12 wt %, about 12 wt % to about 23 wt %, about 23 wt % to about 34 wt %, about 34 wt % to about 45 wt %, about 12 wt % to about 34 wt % or about 30 wt % to about 40 wt %; hemp oil (including, for example, about 2.85% phytocannabinoids other than CBD and about 0.95% CBD), in an amount of about about 0.1 wt % to about 20 wt %, about 0.1 wt % to about 10 wt % or about 0.5 wt % to about 5 wt %; and menthol in an amount of about 0.1 wt % to about 20 wt %, about 1 wt % to about 20 wt %, about 0.1 wt % to about 14 wt %, about 0.1 wt % to about 1 wt % or about 2 wt % to about 9 wt %.

Another embodiment of the present disclosure relates to an anhydrous hydrogel composition, comprising (a) an anhydrous hydrogel including a biocompatible polymer, which can be sodium carboxymethyl cellulose including minimal residual water and a polyalcohol which can be anhydrous glycerin, wherein the combined biocompatible polymer and the polyalcohol is in the range of from about 35 wt % to about 60 wt % and the anhydrous hydrogel can be solid or semi-solid hydrogel having less than 0.5% water; and (b) cannabinoid, for example, CBD, in an amount of about 0.1 wt % to about 20 wt %, about 0.1 wt % to about 10 wt % or about 0.5 wt % to about 5 wt % and menthol in an amount of about 0.1 wt % to about 20 wt %, about 1 wt % to about 20 wt %, about 0.1 wt % to about 14 wt %, about 0.1 wt % to about 1 wt % or about 2 wt % to about 9 wt %.

Another embodiment of the present disclosure relates to an anhydrous hydrogel composition, comprising glycerin about 38.70 w/w %; calcium carbonate about 25.00 w/w %; cellulose gum about 17.03 w/w %; CBD (Hemp) oil about 7.60 w/w %; flavor about 5.00 w/w %; *Cocos nucifera* (coconut oil) about 3.40 w/w %; *Stevia rebaudiana* leaf/stem extract about 2.00 w/w %; menthol about 0.62 w/w %; xanthan gum about 0.35 w/w %; and mentha peperita oil about 0.30 w/w %. Hemp oil contains about 25% CBD, hemp oil breakdown w/w %: phytocannabinoids=about 5.70%, CBD=about 1.9% Total about 7.60%. Unit weight of suppository is about 15 grams, about 1000 mg. CBD and about 1000 mg. menthol. Phytocannabinoids comprise the following: as of 2016, there are 11 subclasses: (1) cannabigerol (CBG); (4) cannabichromene (CBC); (5) cannabinol (CBD); (7) cannabicyclol (CBL); (8) cannabinodiol (CBND); (9) cannabielsoin (CBE); (10) cannabitriol (CBT); and (11) miscellaneous types.

All of the embodiments included here are with the proviso that the sum of ingredients in the exemplary compositions does not exceed 100%.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

In a further embodiment, a kit is disclosed. One example of such a kit is a kit including a composition or unit dose composition of one of the embodiments of the present disclosure including multiple unit doses and instructions for use.

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

Optional ingredients include anti-oxidants, colorants, flavourings and flavour enhancers, preservatives, salivary stimulating agents, cooling agents, co-solvents (including oils), emollients, bulking agents, anti-foaming agents, surfactants, sweetening agents, fillers and taste-masking agents.

Sweetening agents, including pharmaceutically acceptable sweetening agents and sugar-free sweetening agents, can include, for example, saccharin, dextrose, sucrose, lactose, maltose, levulose, aspartame, *Stevia* (e.g., *Stevia rebaudiana* leaf/stem extract), sodium cyclamate, D-tryptophan, dihydrochalcones, acesulfame, monk fruit sweeteners and mixtures thereof. Sweetening agents can be generally used at levels of from about 0.005 wt % to about 5 wt %, by weight of the composition, preferably from about 2 wt % to about 3 wt %.

Fillers, including pharmaceutically acceptable fillers, can include, for example, fumed silica, calcium carbonate, talc, corns starch, clays, methacrylate powder, polyethylene/polypropylene beads, etc. Fillers can be generally used at levels of from about 15 wt % to about 40 wt %, by weight of the composition, preferably from about 20 wt % to about 30 wt %.

Another optional ingredient can be a saliva stimulant. Exemplary saliva stimulants include, but are not limited to, acidic compounds as citric acid, malic acid, lactic acid, ascorbic acid and tartaric acid. In other embodiments, some sweeteners can be used as saliva stimulants, including but not limited to glucose, fructose, xylose, maltose, and lactose. In certain embodiments, a saliva stimulant (e.g., citric acid) can be in an amount of from about 0.1 wt % to about 10 wt %, about 0.1 wt % to about 7 wt %, 0.1 wt % to about 6 wt % or about 2 wt % to about 6 wt %. A unit dose of a saliva stimulant (e.g., citric acid) can be in an amount of from about 10 mg. to about 70 mg. A saliva stimulant may activate the salivary gland, replenish the salivary flow and, thereby, to promote a faster disintegration of the hydrogel and its components and increase the speed with which the actives are administered.

Embodiments of the present disclosure may be delivered for local or systemic administration to a body part of a patient (e.g., person or animal) to be treated with the embodiment, for example, a body or skin surface or an oral cavity surface by placing an embodiment of the present disclosure on an oral cavity surface, for example, an oral mucous membrane or cheek tissue in the oral cavity, in active agent-transmitting relation thereto, the active agents being cannabinoid, for example, phytocannabinoid, and menthol. Embodiments of the present disclosure may also be delivered for local or systemic administration to a human or non-human animal via the digestive system through the oral cavity or rectal region. Alternatively, an embodiment of the present disclosure may be incorporated into a delivery system, such as a unit dose delivery system (e.g. a "patch.""). in manufacturing such systems, the hydrogel adhesive composition may be cast or extruded onto a backing layer or release liner and will serve as the skin-contacting face of the system and act as an active agent reservoir. The delivery system or "patch" can be of a suitable size and shape to fit inside an oral cavity so as to be applied to a surface therein. A suitable size, for example, can include active surface side dimensions ranging from about 0.25 in. to about 1.25 in. and cross-sectional (e.g., thickness) dimensions ranging from about 1/16 in. to about 3/16 in. In manufacturing such systems, the hydrogel adhesive composition may be cast or extruded onto a backing layer or release liner and will serve as the skin-contacting face of the system and act as an active agent reservoir. Alternatively, the hydrogel composition may be used as an active agent reservoir within the interior of such a system, with a conventional skin, oral cavity or other body part contact adhesive laminated thereto to affix the system to a surface on the interior of a patient's oral cavity. In such embodiments including a reservoir, the cannabinoid, for example, CBD, could be in the reservoir and the menthol in the hydrogel housing the reservoir.

A rectal method of delivering embodiments of the present disclosure can include placing the embodiment into the rectal region and in contact with the surrounding tissue such that the therapeutic compounds included in the embodiment pass into the rectal tissues for local or systemic administration of the therapeutic compounds to treat a local or systemic malady.

Embodiments of the present disclosure may be formulated to be immediate and/or modified release. Modified release formulations include delayed-, sustained-, pulsed-, controlled, targeted and programmed release.

Suitable modified release formulations for the purposes of the present disclosure may be adapted, for example, from those described in U.S. Pat. No. 6,106,864. Details of other suitable release technologies such as, for example, high energy dispersions and osmotic and coated particles are to be found in Pharmaceutical Technology On-line, 25(2), 1-14, by Verma et al (2001). The use of chewing gum to achieve controlled release may be adapted from those described in WO 00/35298.

Other embodiments of the present disclosure include a method of relieving pain and/or inflammation by topically administering to the oral cavity, for example, an oral mucous membrane and cheek tissue in the oral cavity, of a mammal in need of such treatment at least one of the compositions disclosed herein. Still other embodiments of the present disclosure include a method of relieving mouth, oral or dental pain by topically administering to the oral cavity, for example, an oral mucous membrane and cheek tissue in the oral cavity, of a mammal in need of such treatment at least one of the compositions disclosed herein. Still other embodiments of the present disclosure include a method of relieving pain and/or inflammation by administering to the oral cavity, for example, an oral mucous membrane and cheek tissue in the oral cavity, of a mammal in need of such treatment at least one of the compositions disclosed herein to a tooth, teeth or other oral tissues or surfaces. Still other embodiments of the present disclosure include a method of relieving mouth, oral or dental pain and/or inflammation by topically administering to the oral cavity, for example, an oral mucous membrane and cheek tissue in the oral cavity, of a mammal in need of such treatment at least one of the compositions disclosed herein to a tooth, teeth or other oral tissues or surfaces.

Other embodiments of the present disclosure include a method of relieving pain and/or inflammation by rectally administering to the rectal cavity of a non-human mammal in need of such treatment at least one of the compositions disclosed herein. Methods of the present disclosure can also include a step-wise method of gradually increasing the dosage for effect, including, for example, breaking a 1000 mg. CBD suppository in half resulting in a 500 mg. CBD suppository for administration.

The embodiments of the present disclosure can include a rectal delivery system (e.g., suppository) having a mass in an amount ranging from about 5 g. to about 10 g., for example, for large animals a mass of about 15 g. including, for example, about 300 mg. of CBD.

An embodiment of the present disclosure can include one of the formulation embodiments of the present disclosure is illustrated in FIG. 1. FIG. 1 includes a suppository 100 to be administered rectally to a non-human, for this embodiment a large animal, e.g., a horse. Suppository 100 includes a body 102 with a generally cylindrical shape and a cylindrical surface 103 and ends 104 and 106. Suppository 100 has a length 108 ranging from about 3 in. to about 4 in. and a generally circular cross-section 110 having a diameter 112 ranging from about 0.5 in. to about 0.75 in., 0.5 in. to about 0.62 in. In the FIG. 1 embodiment show, end 104 has a generally tapered or rounded shape and end 106 has a generally flat shape. Other embodiments of the present disclosure can have both ends with a tapered or rounded shape or both ends with a generally flat shape.

Figure 2A:
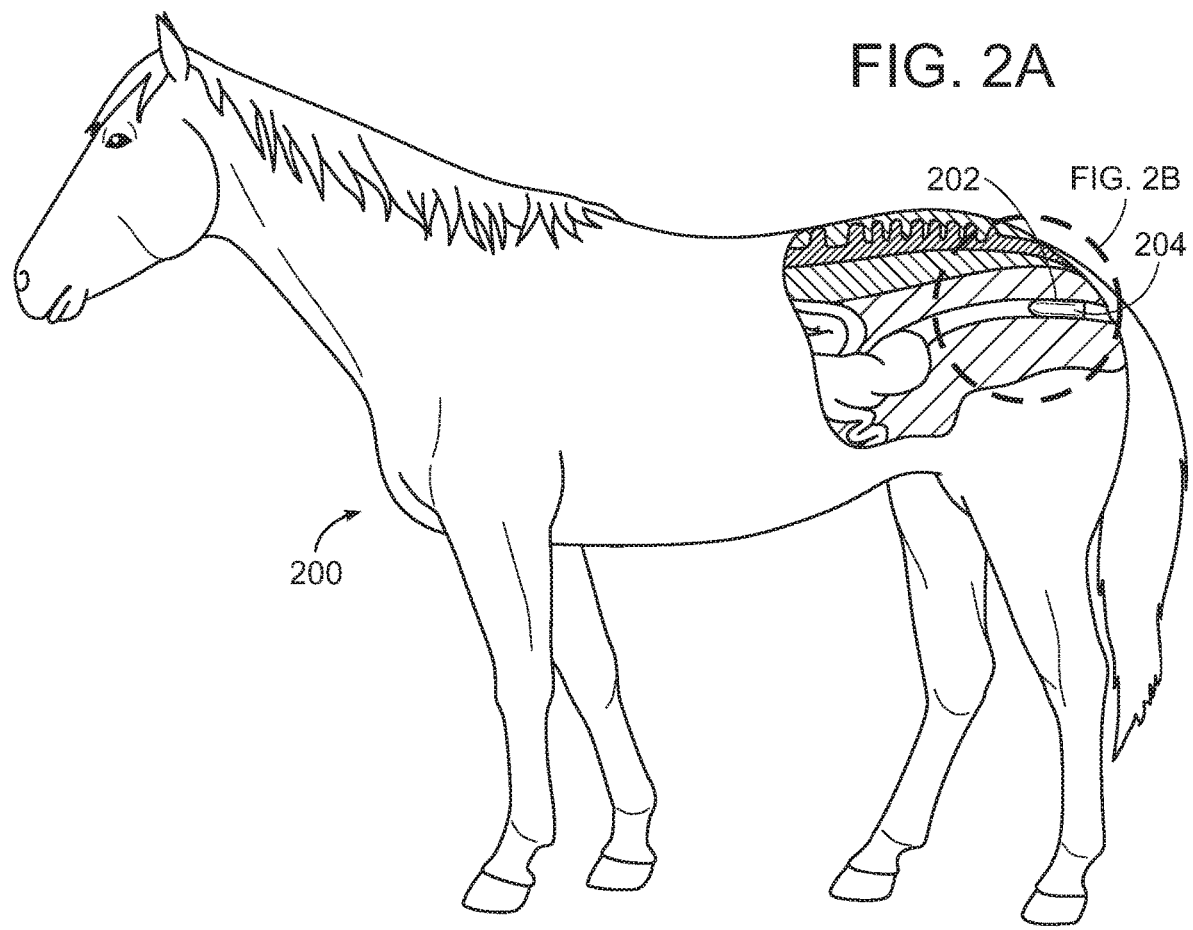
FIGS. 2A and 2B are a side view of a horse with cut-away of the butt end showing the rectal region and a magnified view of the cut-away butt end view.
Figure 2B:
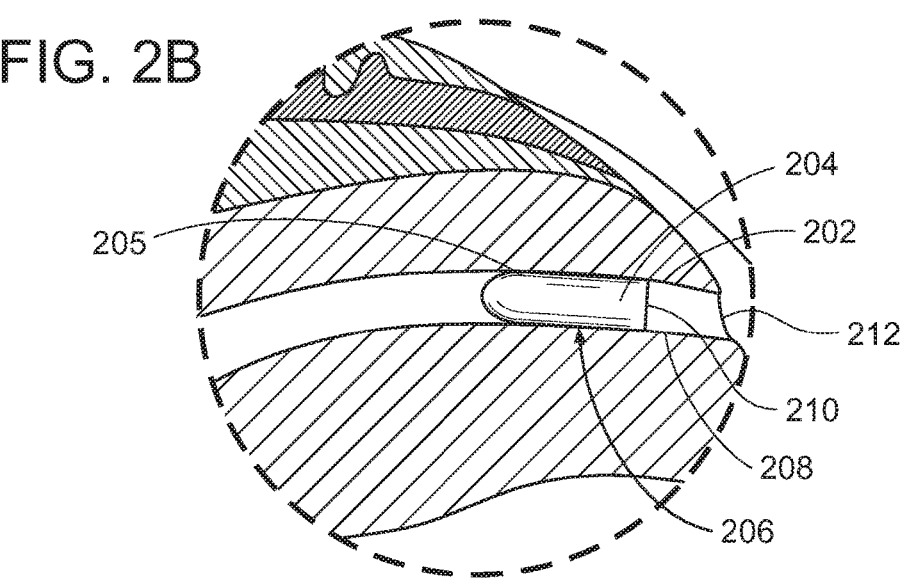

FIGS. 2A and 2B include an illustration of the butt end of a non-human 200 (e.g., a large animal, including for example a horse) including the rectal region 202 of the non-human 200 and one of the suppository embodiments of the present disclosure 204 inserted into the rectal region 202 and positioned at 206 so that the exterior surface 205 of the suppository 204 in contact with the interior wall 208 of the rectal region 202. The position can include the end 210 of the embodiment 204 being about an inch from the end 212 of the rectal region 202. Such a positioning in the rectal region can provide for optimum administration of the agents included therein (e.g., CBD and menthol) for transdermal delivery of those agents in suppository 204 through and into the tissue of the rectal region that the suppository is in contact with to bring about the intended local and/or systemic effect.

It has been surprisingly found that the combination of anhydrous glycerin and sodium carboxymethyl cellulose (CMC) yields an anhydrous material that upon addition of heat (or radiation) is transformed into an anhydrous hydrogel. Unit dosage formulations may be prepared by the addition of 0.1 mg. to 1 g of active agent (depending on the active agent) with glycerin and CMC is likewise transformed into a homogeneous hydrogel upon the addition of heat. These products have less than 0.5% water, more preferably less than 0.4% water, more preferably less than 0.3% water.

Hydrogels of the present disclosure can be subjected to crosslinking methods which enhance the structure and function of the hydrogel. Suitable crosslinking chemical agents include divalent/multivalent metallic cations (e.g., calcium, magnesium, zinc, copper, barium, iron, aluminium, chromium, cerium), phosphates (e.g., pentasodium tripolyphosphate (TPP)), chromates (e.g., dipotassium dichromate), borates (e.g., sodium tetraborate decahydrate), peroxides (e.g., t-butyl hydroperoxide), glycidyl(meth)acrylate, ethylene glycol diglycidyl ether, glutaraldehyde, glycerin, glycols, polyamidoamine epichlorohydrin resin, TMPTA, and the like, and mixtures thereof. Representative crosslinking methods include thermogelation, ionotropic gelation, cryogelation, radiation-induced gelation, chemical gelation, coagulation, crystallization, vulcanization, curing, and combinations thereof.

Another embodiment of the present disclosure relates to anhydrous hydrogels additionally comprising multivalent metal ions (i.e. $Ca++$, $Mg++$, $Fe+++$, $Zn++$ etc) which may be used to modify the cohesive and solubility characteristics as desired. So-called cross-linking resulting from multivalency makes the products more viscous and less hydrophilic.

The anhydrous hydrogels of the present disclosure may further comprise a buffer such as an acid such as citric acid, benzoic acid, salicylic acid, etc.; neutral buffers such as phosphate buffered saline etc.; or alkaline buffers such as borates etc. These buffering agents may be used to adjust for pH sensitive applications.

Another embodiment of the present disclosure relates to a composition of any of the aforesaid embodiments of hydrogel wherein said composition is in thin film, tablet, capsule, oral solution, or oral suspension dosage form.

Formulations suitable for oral administration include solid, semi-solid and liquid systems such as soft or hard capsules containing multi- or nano-particulates, liquids, or powders; lozenges (including liquid-filled); chews; gels; fast dispersing dosage forms; films; ovules; sprays; and buccal/mucoadhesive patches.

The hydrogels of the present disclosure may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Another embodiment of the present disclosure relates to a composition containing particles which have a core containing an active agent or a salt thereof coated with a barrier layer. The barrier layer is formed from a coating liquid that contains a least one water insoluble barrier forming component selected from a group consisting of ethyl cellulose, copolymers of acrylic and methacrylic esters and natural or synthetic waxes, and a plasticizer.

Administration of the compounds of Formula I may be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active agent administered will be dependent on the subject being treated, the severity of the disorder or condition, the rate of administration, the disposition of the compound and the discretion of the prescribing physician. However, an effective dosage is in the range of about 0.001 to about 100 mg. per kg body weight per day, preferably about 1 to about 35 mg./kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of an active agent together with an at least one additional pharmaceutical or medicinal agent, either sequentially or simultaneously.

The present disclosure includes the use of a combination of an active agent and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising an active agent or a pharmaceutically acceptable salt of the compound; (b) a second pharmaceutically active agent; and (c) a pharmaceutically acceptable carrier, vehicle or diluent.

The manufacture of the anhydrous hydrogels may be achieved using a coating line with a heat tunnel, coating a mixture of glycerin (anhydrous) with NaCMC (anhydrous) to a desired thickness and passing the mixture through an oven (under suitable dry conditions so as to retain water free atmosphere) at 105° C. (min) for about 5 minutes (min) until mixture sets. The product may be extruded into molds or thin films. Active agents and additional components are either anhydrous or dehydrated before use. Subject mixture is treated to the same processing parameters as the coating line.

Preferably the composition is extruded directly onto a substrate such as a backing layer or release liner, and then pressed. The thickness of the resulting hydrogel-containing film, for most purposes, will be in the range of about 0.20 mm to about 0.80 mm, more usually in the range of about 0.37 mm to about 0.47 mm.

The hydrogel compositions of the present disclosure may be prepared by solution casting, by admixing the glycerin and CMC at a concentration typically in the range of about 35% to 60% w/w followed by the addition of heat or radiation. The resulting solution is cast onto a substrate such as a backing layer or release liner. Both admixture and casting are preferably carried out at as low temperature as permitted. The substrate coated with the hydrogel film is then baked at a temperature in the range of about 80 degree C. to about 100 degree C., optimally about 90 degree C., for time period in the range of about one to four hours, optimally about two hours.

Films in accordance with the present disclosure are typically prepared by evaporative drying of thin aqueous films coated onto a peelable backing support or paper. This may be done in a drying oven or tunnel, typically a combined coater dryer, or by freeze-drying or vacuuming.

Systems for the topical, transdermal or transmucosal administration of an active agent may comprise: a reservoir containing a therapeutically effective amount of an active agent; an adhesive means for maintaining the system in active agent transmitting relationship to a body surface; and a backing layer as described above, wherein a disposable release liner covers the otherwise exposed surface, protecting such surface during storage and prior to use (also as described above).

The composition will contain a quantity of an active agent effective to provide the desired dosage or effect over a predetermined delivery period.

The compositions of the present disclosure may also include a rate-controlling membrane on the body surface side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

The compositions of the present disclosure may also serve to deliver an active agent using other routes of administration. For example, the compositions may be formulated with excipients, carriers and the like suitable for oral administration of an orally active drug. The compositions may also be used in buccal and sublingual drug delivery, insofar as the compositions can adhere well to moist surfaces within the mouth. In buccal and sublingual systems, hydrolyzable and/or bioerodible polymers may be incorporated into the compositions to facilitate gradual erosion throughout a drug delivery period. Still other types of formulations and drug delivery platforms may be prepared using the present compositions, including implants, rectally administrable compositions, vaginally administrable compositions, and the like.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Example

Rectal delivery (e.g., suppository)—Ingredients: glycerin 38.70 w/w %; calcium carbonate 25.00 w/w %; cellulose gum 17.03 w/w %; CBD (Hemp) oil 7.60 w/w %; flavor 5.00 w/w %; *Cocos nucifera* (coconut oil) 3.40 w/w %; *Stevia rebaudiana* leaf/stem extract 2.00 w/w %; menthol 0.62 w/w %; xanthan gum 0.35 w/w %; and mentha peperita oil 0.30 w/w %. Hemp oil contains 25% CBD, hemp oil breakdown w/w %: phytocannabinoids=5.70%, CBD=1.9% Total 7.60%. Unit weight of suppository is 15 grams, about 1000 mg. CBD and about 1000 mg. menthol. Phytocannabinoids comprise the following: as of 2016, there are 11 subclasses: (1) cannabigerol (CBG); (4) cannabichromene (CBC); (5) cannabinol (CBD); (7) cannabicyclol (CBL); (8) cannabinodiol (CBND); (9) cannabielsoin (CBE); (10) cannabitriol (CBT); and (11) miscellaneous types.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A suppository, comprising:
   a biocompatible polymer in an amount of from about 1 wt % to about 25 wt %;

a polyalcohol in an amount of from about 1 wt % to about 45 wt %;
a veterinary effective amount of at least one cannabinoid; and
a veterinary effective amount of menthol,
wherein the suppository is a solid or semi-solid composition including less than 0.5% water and includes less than 0.3% THC.

2. The suppository of claim 1, wherein the biocompatible polymer is carboxymethyl cellulose and the polyalcohol is glycerin.

3. The suppository of claim 1, wherein the at least one cannabinoid includes CBD.

4. The suppository of claim 1, wherein a unit dose of the at least one cannabinoid in an amount ranging from about 100 mg. to about 1500 mg.

5. The suppository of claim 1, wherein a unit dose of the at least one cannabinoid in an amount ranging from about 5 mg. to about 20 mg.

6. The suppository of claim 1, wherein a unit dose of the menthol in an amount ranging from about 30 mg to about 100 mg.

7. The suppository of claim 1, wherein a unit dose of the menthol in an amount ranging from about 800 mg to about 1100 mg.

8. The suppository of claim 1, wherein veterinary effective amount of at least one cannabinoid includes an anti-inflammatory effective amount.

9. The suppository of claim 1, wherein veterinary effective amount of at least one cannabinoid includes an analgesic effective amount.

10. The suppository of claim 1, wherein veterinary effective amount of menthol includes an anesthetic effective amount.

11. A suppository, comprising:
sodium carboxymethyl cellulose including less than 0.5% residual water and in an amount of from about 1 wt % to about 25 wt %;
glycerin polyalcohol including less than 0.5% and less residual water and in an amount of from about 1 wt % to about 45 wt %;
CBD in an amount of from about 0.1 wt % to about 10 wt %. including a unit dose of CBD in an amount ranging from about 5 mg. to about 1500 mg.; and
menthol is in an amount of from about 0.1 wt % to about 14 wt % including a unit dose of the menthol in an amount ranging from about 30 mg. to about 1500 mg, wherein the suppository includes less than 0.3% THC.

12. The suppository of claim 11, wherein the composition is a unit dose formulation and includes CBD in a unit dose amount of from about 100 mg. to about 1500 mg and menthol in a unit dose amount of from about 800 mg to about 1100 mg.

13. The suppository of claim 11, wherein the composition is a unit dose formulation and includes CBD in a unit dose amount of from about 5 mg. to about 20 mg and menthol in a unit dose amount of from about 30 mg to about 100 mg.

14. A method of treating inflammation in a non-human mammal using a therapeutic suppository, the therapeutic suppository being a unit dose formulation comprising:
sodium carboxymethyl cellulose including less than 0.5% residual water and in an amount of from about 1 wt % to about 25 wt %;
anhydrous glycerin polyalcohol including less than 0.5% and less residual water an in an amount of from about 1 wt % to about 45 wt %;
CBD in a unit dose amount of from about 5 mg. to about 1500 mg.; and
menthol in a unit dose amount of from about 30 mg. to about 1500 mg.,
wherein the suppository includes less than 0.3% THC,
the method comprising administering the therapeutic suppository into a rectal cavity of the non-human mammal.

15. The method of claim 14, wherein the CBD is in an amount of from about 0.1 wt % to about 10 wt %.

16. The method of claim 14, wherein the menthol is in an amount of from about 0.1 wt % to about 14 wt %.

17. The method of claim 14, wherein a unit dose amount of CBD is from about 100 mg. to about 1500 mg. and the menthol is in a unit dose amount of from about 800 mg. to about 1100 mg.

18. The method of claim 14, wherein a unit dose amount of CBD is from about 5 mg. to about 20 mg. and the menthol is in a unit dose amount of from about 30 mg. to about 100 mg.

* * * * *